United States Patent
Yanagita et al.

(10) Patent No.: US 9,029,110 B2
(45) Date of Patent: *May 12, 2015

(54) METHOD FOR PRODUCING FUNCTIONAL MICROBIALLY FERMENTED TEA EXTRACT CONTAINING POLYPHENOL DERIVATIVE

(75) Inventors: Teruyoshi Yanagita, Saga (JP); Kanji Ishimaru, Saga (JP); Takashi Tanaka, Nagasaki (JP); Kazunori Koba, Nagasaki (JP); Hitoshi Miyazaki, Tsukuba (JP); Naohito Aoki, Ichinomiya (JP); Denbei Kawamura, Fukuroi (JP)

(73) Assignees: Kabushiki Kaisha Riverson, Fukuroi-shi, Shizuoka (JP); Saga University, Saga-shi, Saga (JP); Nagasaki Prefectural University Corporation, Sasebo-shi, Nagasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/496,389

(22) PCT Filed: Sep. 17, 2010

(86) PCT No.: PCT/JP2010/066741
§ 371 (c)(1),
(2), (4) Date: May 3, 2012

(87) PCT Pub. No.: WO2011/034218
PCT Pub. Date: Mar. 24, 2011

(65) Prior Publication Data
US 2012/0220650 A1    Aug. 30, 2012

(30) Foreign Application Priority Data
Sep. 18, 2009 (JP) .................. 2009-218055

(51) Int. Cl.
| C12P 1/02 | (2006.01) |
| A61K 8/49 | (2006.01) |
| A23K 1/00 | (2006.01) |
| A23K 1/16 | (2006.01) |
| A23L 1/30 | (2006.01) |
| A61Q 19/00 | (2006.01) |
| A61K 8/97 | (2006.01) |

(52) U.S. Cl.
CPC .................. *A61K 8/498* (2013.01); *A23K 1/007* (2013.01); *A23K 1/1618* (2013.01); *A23K 1/1646* (2013.01); *A23L 1/3002* (2013.01); *A61Q 19/00* (2013.01); *A23K 1/1612* (2013.01); *A61K 8/97* (2013.01); *A61K 2800/522* (2013.01); *A61K 2800/85* (2013.01)

(58) Field of Classification Search
None
See application file for complete search history.

(56) References Cited

U.S. PATENT DOCUMENTS

| 2,785,979 | A | * | 3/1957 | Mitchell | 426/597 |
| 2,863,775 | A | * | 12/1958 | Perech | 426/49 |
| 5,820,901 | A | * | 10/1998 | Nicolas et al. | 426/49 |
| 5,863,581 | A | * | 1/1999 | Barrett et al. | 426/250 |
| 5,879,683 | A | * | 3/1999 | Hamilton-Miller | 424/195.11 |
| 5,888,571 | A | * | 3/1999 | Choi | 426/431 |
| 5,993,867 | A | * | 11/1999 | Rohdewald | 426/96 |
| 6,063,428 | A | * | 5/2000 | Ekanayake et al. | 426/597 |
| 6,068,862 | A | * | 5/2000 | Ishihara et al. | 426/2 |
| 6,113,965 | A | * | 9/2000 | Goodsall et al. | 426/425 |
| 6,319,523 | B1 | * | 11/2001 | Zhou | 424/725 |
| 2004/0018273 | A1 | * | 1/2004 | David et al. | 426/49 |
| 2004/0028793 | A1 | * | 2/2004 | Inaoka et al. | 426/590 |
| 2005/0084566 | A1 | * | 4/2005 | Bavan | 426/49 |
| 2005/0158437 | A1 | * | 7/2005 | Itaya et al. | 426/534 |
| 2007/0166407 | A1 | * | 7/2007 | Tanaka et al. | 424/727 |
| 2008/0121108 | A1 | * | 5/2008 | Vicker | 99/279 |

FOREIGN PATENT DOCUMENTS

| JP | 62257343 | A | * | 11/1987 | ........... A23F 3/06 |
| JP | 2005-333929 | A | | 12/2005 | |
| JP | 2008-263831 | A | | 11/2008 | |
| JP | 2009-28010 | A | | 2/2009 | |

OTHER PUBLICATIONS

Finger et al., J. Sci. Food Agric., 55:313-321 (1991).*
Kiehne et al., Z. Lebensm Unters Forsch, 202:48-54 (1996).*
Zhou et al., J. Agric. Food Chem., 53:8614-8617 (2005).*
Kanji Ishimaru, "Analysis and functional estimation of processed metabolites of plant polyphenols as food ingredients", Mar. 25, 2009, pp. 1-4.

* cited by examiner

*Primary Examiner* — Blaine Lankford
*Assistant Examiner* — Thomas J Visone
(74) *Attorney, Agent, or Firm* — Manabu Kanesaka

(57) ABSTRACT

A functional microbially fermented tea extract containing a novel polyphenol derivative and a method for producing the same are provided. A functional microbially fermented tea extract containing various extracts and a novel polyphenol derivative is produced by subjecting, to an extraction treatment, a microbially fermented tea leaf obtained by culturing one species selected from *Aspergillus* sp. (PK-1), *Aspergillus oryzae* (NBRS 4214) sp. (AO-1), *Aspergillus awamori* (NBRS 4122) sp. (SK-1), and *Eurotium* sp. (KA-1) with a tea leaf. Furthermore, for example, a functional fermented tea extract enriched with a novel polyphenol derivative is produced.

3 Claims, 11 Drawing Sheets

FIG. 3
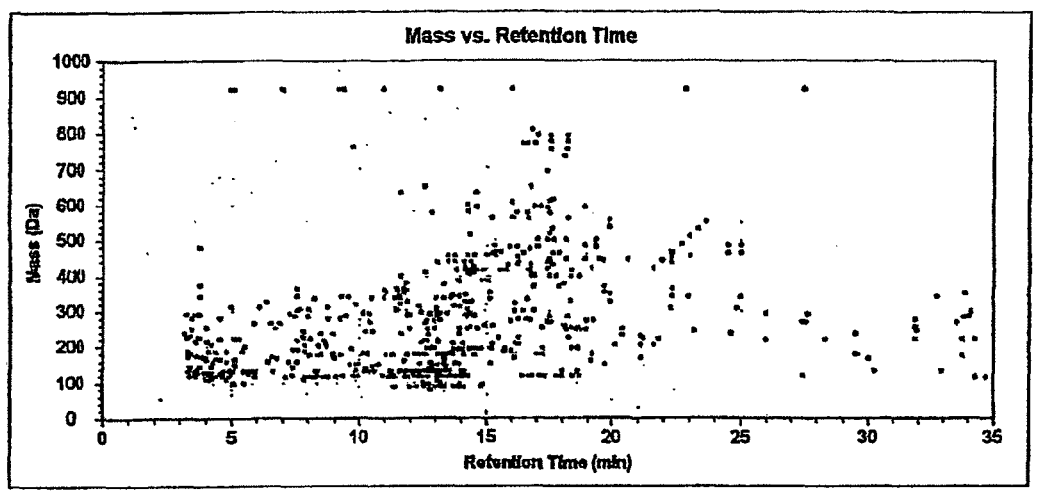
A: Plot of components of 1000 or lower in molecular weight contained in 5 tea types
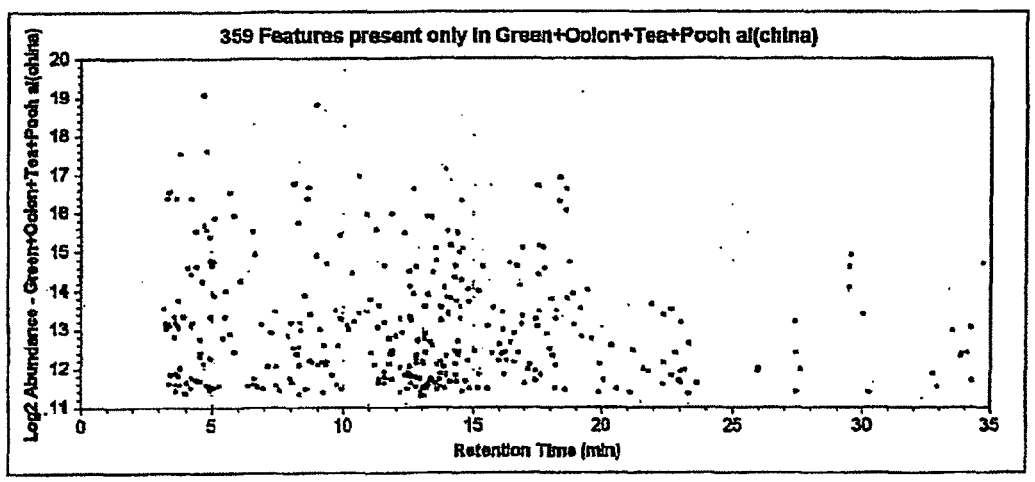
B: Plot of components contained only in 4 tea types other than RS tea

FIG. 4
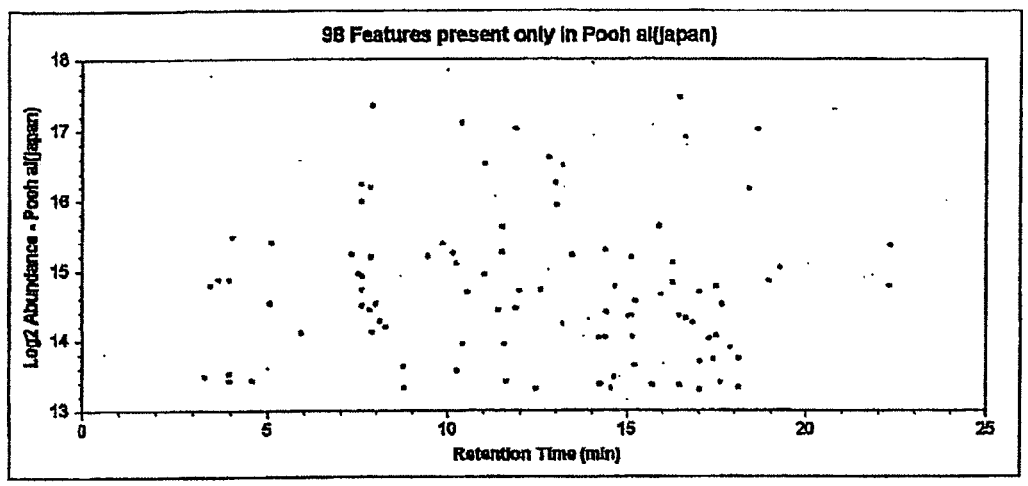
A: Plot of components contained only in RS tea
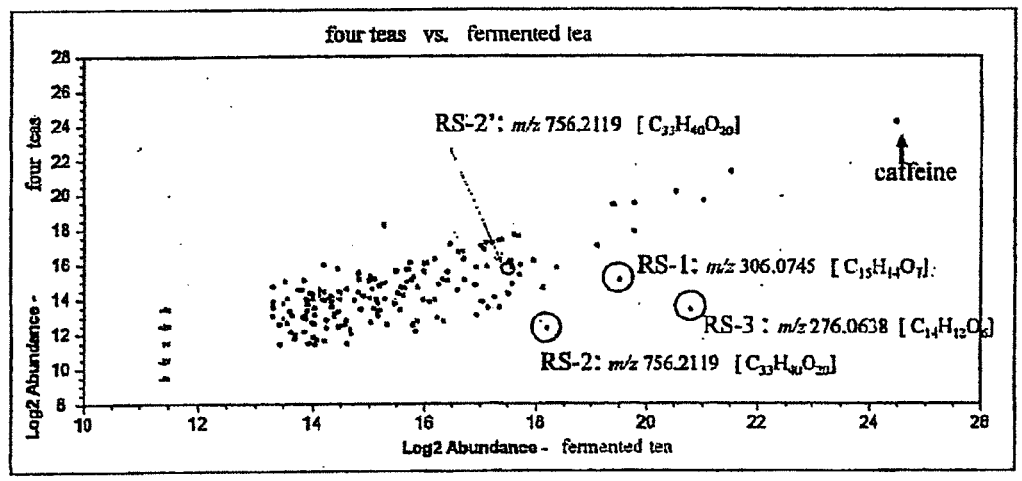
B: Correlation plot of components contained in RS tea (abscissa) and the other 4 tea types (ordinate).

FIG. 5

Adiponectin

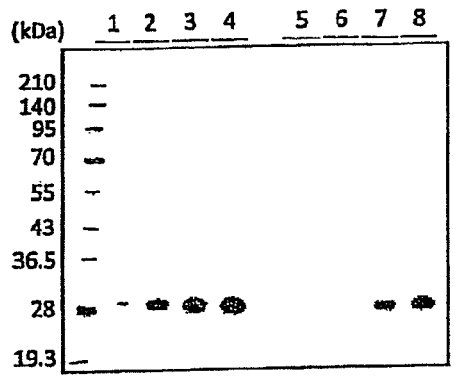

First run

| Lane | Sample name | Integrated value | Relative value |
|---|---|---|---|
| 1 | Teadenol A 8 h | 3058 | 118 |
| 2 | Teadenol A 24 h | 8878 | 288 |
| 3 | Teadenol A 32 h | 14163 | 198 |
| 4 | Teadenol A 48 h | 17616 | 172 |
| 5 | 100% DMSO 8 h | 2587 | 100 |
| 6 | 100% DMSO 24 h | 3017 | 100 |
| 7 | 100% DMSO 32 h | 7151 | 100 |
| 8 | 100% DMSO 48 h | 10256 | 100 |

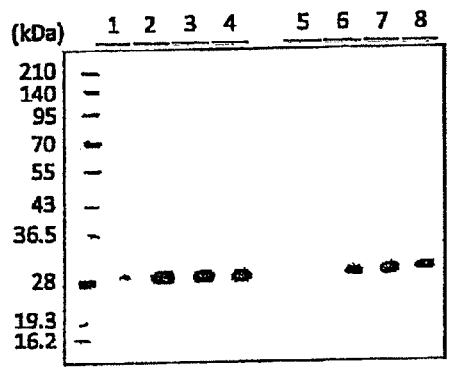

Second run

| Lane | Sample name | Integrated value | Relative value |
|---|---|---|---|
| 1 | Teadenol A 8 h | 3726 | 148 |
| 2 | Teadenol A 24 h | 13674 | 205 |
| 3 | Teadenol A 32 h | 11269 | 125 |
| 4 | Teadenol A 48 h | 9966 | 143 |
| 5 | 100% DMSO 8 h | 2519 | 100 |
| 6 | 100% DMSO 24 h | 6657 | 100 |
| 7 | 100% DMSO 32 h | 9037 | 100 |
| 8 | 100% DMSO 48 h | 6951 | 100 |

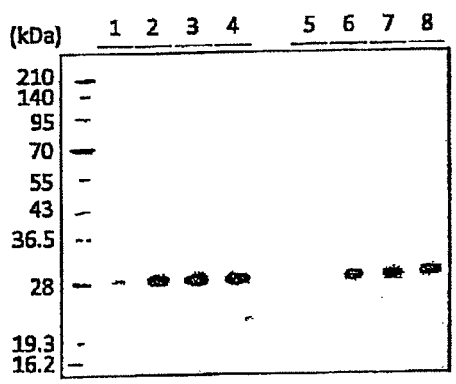

Third run

| Lane | Sample name | Integrated value | Relative value |
|---|---|---|---|
| 1 | Teadenol A 8 h | 3261 | 232 |
| 2 | Teadenol A 24 h | 11369 | 151 |
| 3 | Teadenol A 32 h | 12330 | 137 |
| 4 | Teadenol A 48 h | 12348 | 128 |
| 5 | 100% DMSD 8 h | 1408 | 100 |
| 6 | 100% DMSO 24 h | 7505 | 100 |
| 7 | 100% DMSO 32 h | 8983 | 100 |
| 8 | 100% DMSO 48 h | 9626 | 100 |

FIG. 7
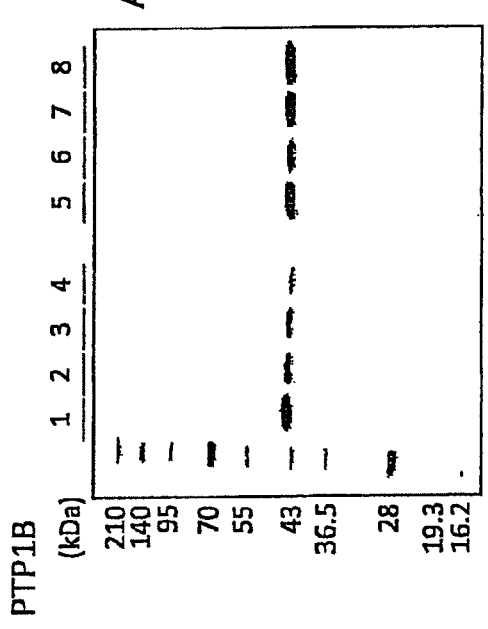
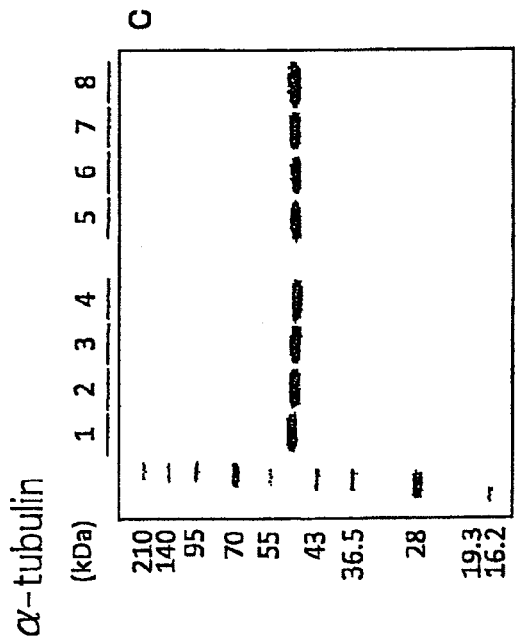

FIG. 8
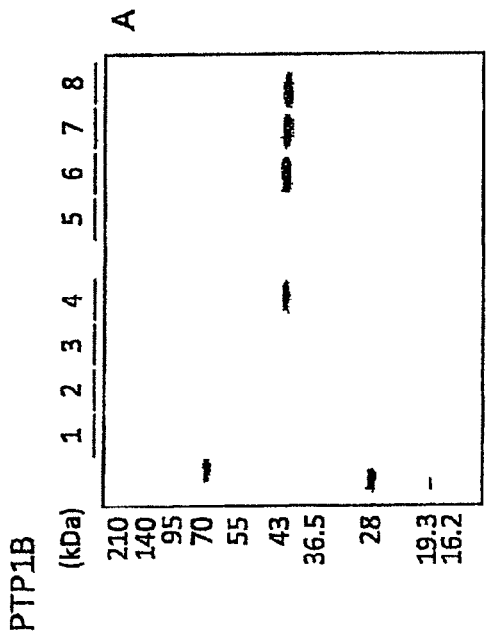
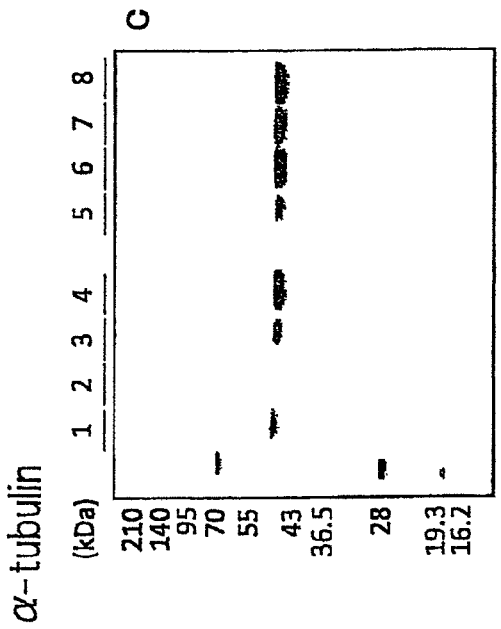
PTP1B
| Lane | Sample name | Integrated value | Relative value |
|---|---|---|---|
| 1 | Teadenol A 8 h | 1563 | 80 |
| 2 | Teadenol A 24 h | 265 | 3 |
| 3 | Teadenol A 32 h | 2095 | 23 |
| 4 | Teadenol A 48 h | 6217 | 71 |
| 5 | 100% DMSO 8 h | 1945 | 100 |
| 6 | 100% DMSO 24 h | 10226 | 100 |
| 7 | 100% DMSO 32 h | 9188 | 100 |
| 8 | 100% DMSO 48 h | 8809 | 100 |
α-tubulin
| Lane | Sample name | Integrated value | Relative value |
|---|---|---|---|
| 1 | Teadenol A 8 h | 6328 | 111 |
| 2 | Teadenol A 24 h | 1636 | 12 |
| 3 | Teadenol A 32 h | 5915 | 53 |
| 4 | Teadenol A 48 h | 14614 | 104 |
| 5 | 100% DMSO 8 h | 5697 | 100 |
| 6 | 100% DMSO 24 h | 13882 | 100 |
| 7 | 100% DMSO 32 h | 11263 | 100 |
| 8 | 100% DMSO 48 h | 14001 | 100 |

FIG. 9
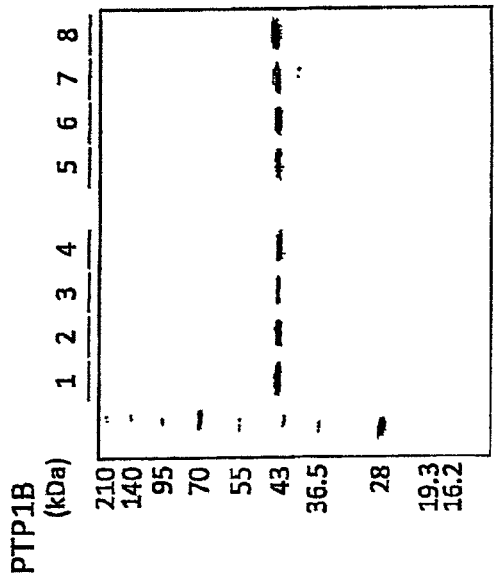
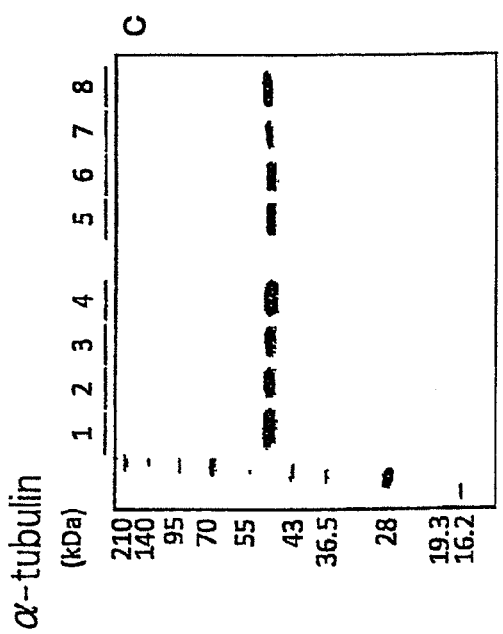

FIG. 10

A. First run

| Lane | Sample name | PTP1B Relative value | α-tubulin Relative value | Corrected value (PTP1B/α-tubulin*100) |
|---|---|---|---|---|
| 1 | Teadenol A 8 h | 81 | 106 | 0.77 |
| 2 | Teadenol A 24 h | 94 | 115 | 0.82 |
| 3 | Teadenol A 32 h | 44 | 111 | 0.40 |
| 4 | Teadenol A 48 h | 28 | 80 | 0.35 |
| 5 | 100% DMSO 8 h | 100 | 100 | 1.00 |
| 6 | 100% DMSO 24 h | 100 | 100 | 1.00 |
| 7 | 100% DMSO 32 h | 100 | 100 | 1.00 |
| 8 | 100% DMSO 48 h | 100 | 100 | 1.00 |

B. Second run

| Lane | Sample name | PTP1B Relative value | α-tubulin Relative value | Corrected value (PTP1B/α-tubulin*100) |
|---|---|---|---|---|
| 1 | Teadenol A 8 h | 80 | 111 | 0.72 |
| 2 | Teadenol A 24 h | 3 | 12 | 0.22 |
| 3 | Teadenol A 32 h | 23 | 53 | 0.43 |
| 4 | Teadenol A 48 h | 71 | 104 | 0.68 |
| 5 | 100% DMSO 8 h | 100 | 100 | 1.00 |
| 6 | 100% DMSO 24 h | 100 | 100 | 1.00 |
| 7 | 100% DMSO 32 h | 100 | 100 | 1.00 |
| 8 | 100% DMSO 48 h | 100 | 100 | 1.00 |

C. Third run

| Lane | Sample name | PTP1B Relative value | α-tubulin Relative value | Corrected value (PTP1B/α-tubulin*100) |
|---|---|---|---|---|
| 1 | Teadenol A 8 h | 117 | 199 | 0.59 |
| 2 | Teadenol A 24 h | 92 | 132 | 0.70 |
| 3 | Teadenol A 32 h | 76 | 178 | 0.43 |
| 4 | Teadenol A 48 h | 75 | 133 | 0.56 |
| 5 | 100% DMSO 8 h | 100 | 100 | 1.00 |
| 6 | 100% DMSO 24 h | 100 | 100 | 1.00 |
| 7 | 100% DMSO 32 h | 100 | 100 | 1.00 |
| 8 | 100% DMSO 48 h | 100 | 100 | 1.00 |

D. Summary

| 3 runs | Sample name | Mean | Standard error |
|---|---|---|---|
| 1 | Teadenol A 8 h | 69.22 | 5.37 |
| 2 | Teadenol A 24 h | 57.88 | 18.28 |
| 3 | Teadenol A 32 h | 41.90 | 1.20 |
| 4 | Teadenol A 48 h | 53.01 | 9.55 |
| 5 | 100% DMSO 8 h | 100.00 | 9.36 |
| 6 | 100% DMSO 24 h | 100.00 | 10.21 |
| 7 | 100% DMSO 32 h | 100.00 | 4.54 |
| 8 | 100% DMSO 48 h | 100.00 | 28.84 |

METHOD FOR PRODUCING FUNCTIONAL MICROBIALLY FERMENTED TEA EXTRACT CONTAINING POLYPHENOL DERIVATIVE

RELATED APPLICATIONS

The present application is National Phase of International Application No. PCT/JP2010/066741 filed Sep. 17, 2010, and claims priority from Japanese Application No. 2009-218052, filed Sep. 18, 2009.

TECHNICAL FIELD

The present invention relates to a method for producing functional microbially fermented tea extract containing a novel polyphenol derivative.

BACKGROUND ART

Conventionally known polyphenol derivatives include catechin, epicatechin gallate, epigallocatechin, epigallocatechin gallate, and gallocatechin gallate contained in tea leaves, which have been used as physiologically functional substances exhibiting various physiological activities.

Moreover, it has also been proposed that a post-fermented tea leaf containing 4-ethenyl-1,2-dimethoxybenzene, aceteugenol, or isoeugenol is produced by fermenting a tea leaf with a microbe PK-1 belonging to the genus *Aspergillus* (FERM P-21280) or a microbe KA-1 belonging to the genus *Eurotium* (FERM P-21291) (Japanese Patent Laid-Open No. 2008-263831).

Patent Literature 1: Japanese Patent Laid-Open No. 2008-263831

SUMMARY OF INVENTION

Technical Problem

An object of the present invention is to provide a functional microbially fermented tea extract containing a novel substance exhibiting physiologically active effects, which is obtained from a fermented tea leaf.

Solution to Problem

The present inventors have found that a novel polyphenol derivative represented by the following general formula (1) is isolated by subjecting, to an extraction treatment, a microbially fermented tea leaf obtained by culturing one species selected from *Aspergillus* sp. (PK-1) (FERM P-21280), *Aspergillus oryzae* (NBRS 4214) sp. (AO-1), *Aspergillus awamori* (NBRS 4122) sp. (SK-1), and *Eurotium* sp. (KA-1) (FERM P-21291) with a tea leaf:

[Formula 1]

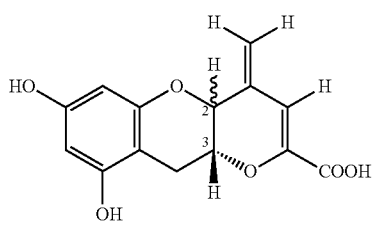

(1)

The present invention has been completed on the basis of these findings and relates to:

1. a functional microbially fermented tea extract containing various extracts and a polyphenol derivative represented by the following general formula (1), obtained by subjecting, to an extraction treatment, a microbially fermented tea leaf obtained by culturing one species selected from *Aspergillus* sp. (PK-1) (FERM P-21280), *Aspergillus oryzae* (NBRS 4214) sp. (AO-1), *Aspergillus awamori* (NBRS 4122) sp. (SK-1), and *Eurotium* sp. (KA-1) (FERM P-21291) with a tea leaf, or a functional fermented tea extract enriched with a polyphenol derivative represented by the following general formula (1) by adding the polyphenol derivative represented by the following general formula (1) to the fermented tea extract:

[Formula 2]

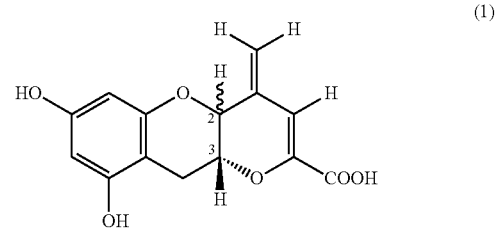

(1)

and 2. a method for producing a functional microbially fermented tea extract containing various extracts and a polyphenol derivative represented by the following general formula (1), comprising subjecting, to an extraction treatment, a microbially fermented tea leaf obtained by culturing one species selected from *Aspergillus* sp. (PK-1) (FERM P-21280), *Aspergillus oryzae* (NBRS 4214) sp. (AO-1), *Aspergillus awamori* (NBRS 4122) sp. (SK-1), and *Eurotium* sp. (KA-1) (FERM P-21291) with a tea leaf, or for producing a functional fermented tea extract enriched with a polyphenol derivative represented by the following general formula (1), comprising adding the polyphenol derivative represented by the following general formula (1) to the fermented tea extract:

[Formula 3]

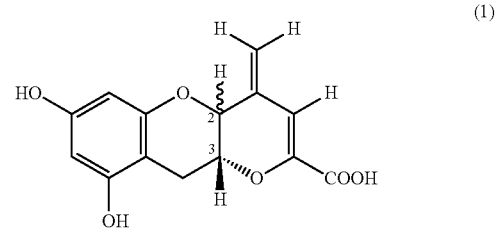

(1)

The present invention further relates to the functional microbially fermented tea extract and the method for producing the functional microbially fermented tea extract, wherein the various extracts obtained comprised comprise gallic acid, gallocatechin, epigallocatechin, catechin, epicatechin, epigallocatechin gallate, epicatechin gallate, and kaempferol triglycoside, and a processed food, etc., comprising the functional microbially fermented tea extract.

Advantageous Effects of Invention

The present invention can provide a functional microbially fermented tea extract that has, for example, the functions of decreasing visceral fat and increasing adiponectin and exhibits specific physiologically active effects, and a food, feed, etc., comprising this extract. An extract enriched with a compound of the general formula (1) has higher, useful bioactivities and can be applied to various uses.

BRIEF DESCRIPTION OF DRAWINGS

FIG. 3 is an LC-TOF/MS analysis plot of components contained in various tea types (5 types: green tea, oolong tea, black tea, pu-erh tea made in China, and RS tea).
- A: Plot of components of 1000 or lower in molecular weight contained in 5 tea types, and
- B: Plot of components contained only in 4 tea types other than RS tea.

FIG. 4 is an LC-TOF/MS analysis plot of components contained in various tea types (5 types: green tea, oolong tea, black tea, pu-erh tea made in China, and RS tea).
- A: Plot of components contained only in RS tea, and
- B: Correlation plot of components contained in RS tea (abscissa) and the other 4 tea types (ordinate).

FIG. 5 is assay results of the adiponectin secretion promoting activity of teadenol A.
- A and B: Results of the first run,
- C and D: Results of the second run, and
- E and F: Results of the third run.
- A, C, and E: Western blot pattern.

FIG. 7 is assay results (first run) of the PTP1B expression inhibitory activity of teadenol A.
- A and B: Results of assay on PTP1B expression level, and
- C and D: Results of assay on the amount of α-tubulin.
- A and C: Western blot pattern.

FIG. 8 is assay results (second run) of the PTP1B expression inhibitory activity of teadenol A.
- A and B: Results of assay on PTP1B expression level, and
- C and D: Results of assay on the amount of α-tubulin.
- A and C: Western blot pattern.

FIG. 9 is assay results (third run) of the PTP1B expression inhibitory activity of teadenol A.
- A and B: Results of assay on PTP1B expression level, and
- C and D: Results of assay on the amount of α-tubulin.
- A and C: Western blot pattern.

FIG. 10 is assay results of the PTP1B expression inhibitory activity of teadenol A.
- A: Results of assay on PTP1B expression level and the amount of α-tubulin (first run),
- B: Results of assay on PTP1B expression level and the amount of α-tubulin (second run),
- C: Results of assay on PTP1B expression level and the amount of α-tubulin (third run), and
- D: Summary of results of three runs.

It shows the relationship between a PTP1B expression level and a time lapsed after addition of teadenol A.

DESCRIPTION OF EMBODIMENTS

Aspergillus sp. (PK-1) (FERM P-21280) described above has been registered as Accession No. FERM P-21280, as described in Japanese Patent Laid-Open No. 2008-263831 above related to the application of the present applicants.

The isolated strain of Aspergillus sp. (PK-1) (FERM P-21280) was originally deposited and accepted as a domestic deposition on Mar. 26, 2007 and the accession number FERM P-21280 was assigned, and deposited and accepted under the provisions of Budapest Treaty on Dec. 27, 2010 and the accession number FERM BP-11296 was assigned, with the International Patent Organism Depositary, National Institute of Advanced Industrial Science and Technology (AIST) (Tsukuba Central 6, 1-1, Higashi 1-chome, Tsukuba-shi, Ibaraki-ken 305-8566 JAPAN).

Moreover, Aspergillus oryzae (NBRS 4214) sp. (AO-1), Aspergillus awamori (NBRS 4122) sp. (SK-1), or Eurotium sp. (KA-1) (FERM P-21291) is also already known in the art.

The isolated strain of Eurotium sp. (KA-1) (FERM P-21291) was originally deposited and accepted as a domestic deposition on Apr. 11, 2007 and the accession number FERM P-21291 was assigned, and deposited and accepted under the provisions of Budapest Treaty on Dec. 27, 2010 and the accession number FERM BP-11297 was assigned, with the International Patent Organism Depositary, National Institute of Advanced Industrial Science and Technology (AIST) (Tsukuba Central 6, 1-1, Higashi 1-chome, Tsukuba-shi, Ibaraki-ken 305-8566 JAPAN).

A polyphenol derivative and various extracts according to the present invention are obtained by a production method described above. They are confirmed by examining the extract thus extracted from the microbially fermented tea leaf, by HPLC analysis.

Figure 1:
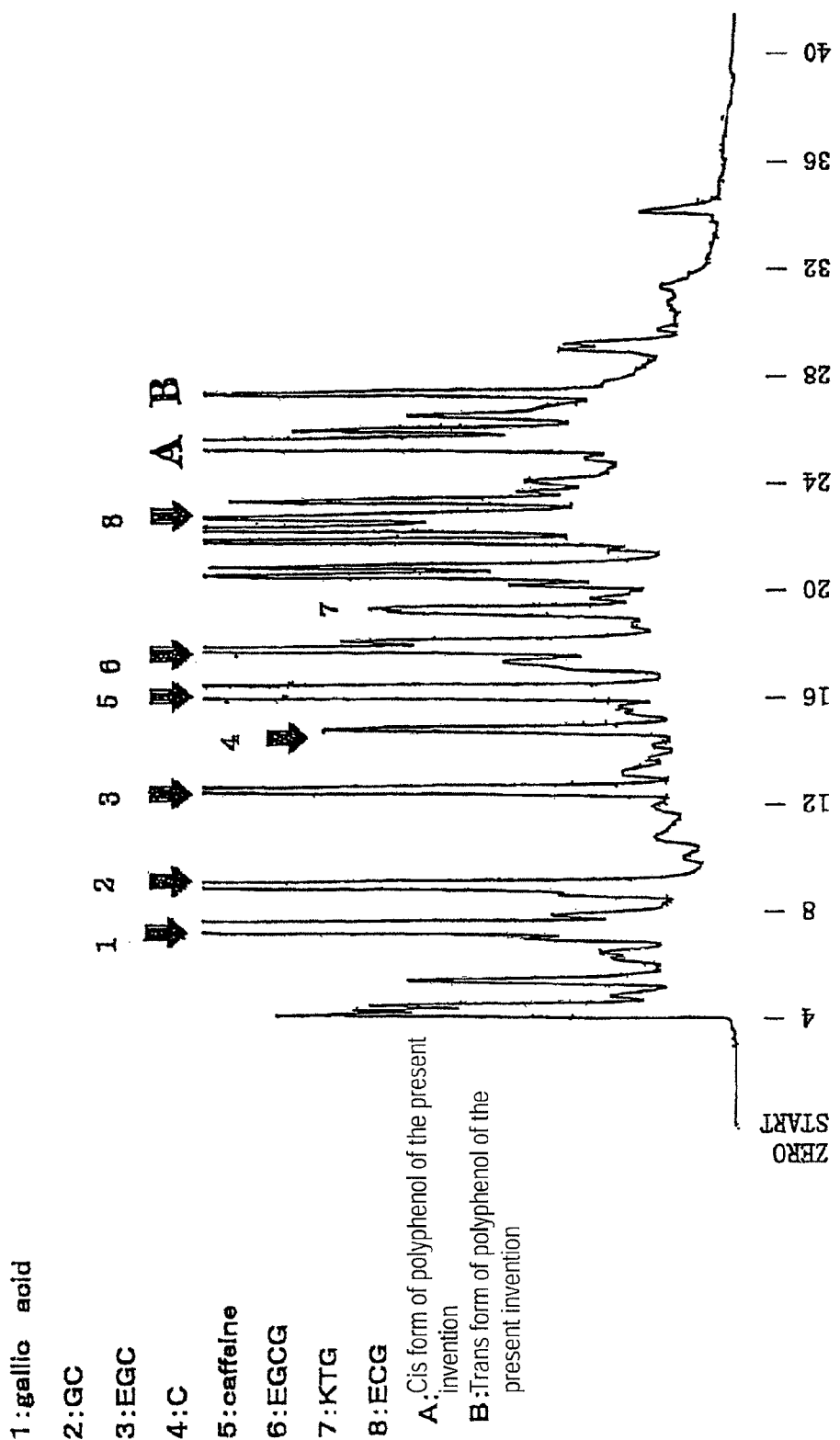
FIG. 1 is an analysis diagram showing results of HPLC analysis on a microbially fermented tea extract of Example of the present invention.

FIG. 1 of the drawings shows an example of an analysis diagram showing results of analyzing the extract by HPLC analysis. Furthermore, in this analysis diagram, 1 shows the peak of gallic acid; 2 shows the peak of gallocatechin (GC); 3 shows the peak of epigallocatechin (EGC); 4 shows the peak of catechin (C); 5 shows the peak of caffeine; 6 shows the peak of epigallocatechin gallate (EGCG); 7 shows the peak of kaempferol triglycoside (KTG); 8 shows the peak of epicatechin gallate (ECG); A shows the peak of a cis form of a polyphenol derivative according to the present invention; and B shows the peak of a trans form of a polyphenol derivative according to the present invention.

Furthermore, the polyphenol derivative of the present invention has stereoisomers, which exist in two forms: cis and trans forms, as described above. The cis form is represented by the following structural formula (2):

[Formula 4]

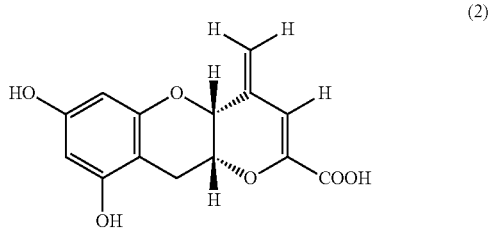

(2)

Moreover, the trans form is represented by the following structural formula (3):

[Formula 5]

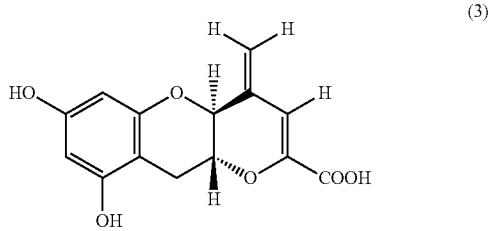

(3)

For producing the polyphenol derivative and various extracts of the present invention, any type or state of a leaf from tea (*Camellia sinensis* L.) can generally be used as a culture material. For example, first-grade tea, second-grade tea, or even third-grade tea are used.

Moreover, for producing the microbially fermented tea leaf of the present invention, it is preferred to perform a heat treatment before the fermentation treatment for the purpose of preventing oxidation reaction, etc., mediated by enzymes contained in the tea leaf. A tea leaf obtained by directly subjecting a harvested tea leaf to the heat treatment may be used. The heating method is not particularly limited, and any method or apparatus such as a direct heat method using a kettle, heating using various dryers with electricity, gas, or the like as a heat source, steam heat dryers using steam, drying in the sun, may be used as long as it is a method that can deactivate the enzymes by the heat treatment of the tea leaf.

For example, a tea leaf after fixation, a tea leaf after primary rolling and drying, a tea leaf after crumpling, a tea leaf after secondary rolling and drying, a tea leaf after final rolling and drying, or a dried tea leaf in the conventional production process of Sencha (green tea of middle grade) is used as the tea leaf whose enzymes have been deactivated by heating, in the production of the microbially fermented tea leaf of the present invention.

For the microbial fermentation treatment of the tea leaf, it is required to keep the raw material tea leaf under conditions where fermentation with the microbe inoculated thereinto proceeds. A tea leaf whose water content has been adjusted to approximately 15 to 80% by weight of water is used. Preferably, a tea leaf containing 30 to 40% by weight of water is used. For example, since the tea leaf after secondary rolling and drying contains approximately 25 to 40% by weight of water, the tea leaf after secondary rolling and drying is used in the fermentation treatment of the present invention without adjusting its water content.

The fermentation temperature in the present invention is preferably approximately 15 to 50° C. The fermentation treatment is usually performed for 1 to 60 consecutive days, preferably 3 to 15 consecutive days, which are however shorter than the period required for the conventional production of post-fermented tea. Thus, efficient production can be achieved. It is preferred to carry out the microbial fermentation treatment by appropriately selecting the water content of the tea leaf, the fermentation temperature, the fermentation period, etc. so that the yields of the useful components of the present invention are increased as much as possible during the microbial fermentation treatment.

This tea leaf is usually sterilized before the culture, and the sterilization is carried out, for example, by sterilizing the teal leaf at 121° C. for 15 minutes in an autoclave.

The production method of the present invention is performed by drying the cultured tea leaf after the culture.

In the extraction method, water, a hydrophilic organic solvent, or an aqueous solution of this hydrophilic organic solvent is generally used. Preferably, an aqueous ethanol solution, ethanol, or water is used.

For example, a method using column chromatography is used for obtaining the polyphenol derivative of the present invention and various extracts from the extract obtained by the extraction treatment.

A novel polyphenol derivative having the chemical structure represented by the general formula (1) (compound (1)) is obtained, for example, by: subjecting a fermented tea leaf obtained by culturing the predetermined microbe (including *Aspergillus* sp. (PK-1)) with a tea leaf, to an extraction treatment to isolate a polyphenol derivative represented by the general formula (1); and/or contacting (−)-epigallocatechin 3-O-gallate [EGCG] and/or a C-2 epimer thereof with *Aspergillus* sp. (PK-1) or the like or an extract thereof to form a polyphenol derivative represented by the general formula (1). An extract enriched with the compound (1) can be obtained by adding the compound (1), i.e., teadenol A and/or teadenol B, to various extracts (including an extract containing a concentrated compound (1)) obtained by subjecting the fermented tea leaf to an extraction treatment. The fermented tea extract enriched with the compound (1) has the advantage that, for example, bioactivities exerted by the compound (1) can be further expected.

The novel polyphenol derivative having the chemical structure represented by the general formula (1) (compound (1)) is a substance having useful physiological activities/bioactivities and has been confirmed to have, for example, an adiponectin secretion promoting effect and a protein tyrosine phosphatase-1B (PTP1B) expression inhibitory effect. Thus, the extract containing the compound (1), particularly, the extract enriched with the compound (1) or the extract containing the concentrated compound (1), is promising in various uses such as pharmaceuticals, food ingredients, animal feed ingredients, cosmetic ingredients, and assay reagents.

Adiponectin is known to be a secretory protein secreted from adipocytes. Its blood concentration is much larger than that of general hormones and allegedly reaches μg/ml orders. Diverse effects such as enhanced insulin sensitivity based on the activation of liver AMPK (AMP-activated protein kinase), inhibition of arteriosclerosis, an anti-inflammatory effect, and inhibition of myocardial hypertrophy have been reported as the effects of adiponectin. The blood adiponectin concentration is known to inversely correlate with the amount of visceral fat. Although much remains to be elucidated for the mechanism thereof, for example, TNFα, which is increased in adipose tissues in obesity, is considered to be partially responsible therefor.

It has been reported that: more obese individuals have the lower amount of adiponectin secreted; visceral fat accumulation leads to the decreased amount of adiponectin secreted; the progression of arteriosclerosis can be delayed by keeping the amount of blood adiponectin at a certain level or larger; and such adiponectin exhibits an oxidative stress inhibitory effect. Thus, by use of its adiponectin secretion promoting activity, the extract containing the compound (1) of the present invention can be used in the improvement of diabetes mellitus, the prevention of the onset of diabetes mellitus, anticancer use, the improvement of lifestyle-related disease (metabolic syndrome), the prevention of the onset of lifestyle-related disease, the improvement of obesity, the improvement of hypertension, the prevention of the onset of hypertension, the improvement of arteriosclerosis, the prevention of the onset of arteriosclerosis, etc., and is useful as a pharmaceutical, a food or a food additive, a seasoning, a health supplement, a supplement, a functional food, animal feed, a cosmetic or a cosmetic additive, a reagent for drug development, a reagent for bioactivity assay, etc.

Protein tyrosine phosphatases (PTPs) are a group of enzymes (tyrosine dephosphorylating enzyme group) that specifically dephosphorylate proteins having a phosphorylated tyrosine residue, and are important molecules controlling intracellular signal transduction. Therefore, these enzymes are considered to participate in many diseases, and PTP1B has been reported as typical PTP thereof. PTP1B was identified from human placenta in 1988 and stepped into the limelight due to its involvement in insulin resistance, diabetes mellitus, or obesity. Since SNPs in the nucleotide sequence of PTP1B influence insulin sensitivity or blood glucose concentrations, PTP1B is also considered to play a central role in the regulation thereof. The main tissues that regulate blood glucose concentrations by insulin are the liver, muscles, and fats. The overexpression or knockout of PTP1B specific for these tissues or cells results in observable change in insulin sensitivity or blood glucose concentration. Considering that the expression level of PTP1B is increased by approximately 7 times, particularly, in the adipose tissues of mouse models of obesity loaded with high fat diets compared with usual mice and the expression level is approximately 1.5 times to 2 times in the liver or muscles, insulin resistance associated with obesity may probably be influenced greatly by reduction in insulin sensitivity caused by the increased expression of PTP1B in adipocytes.

Against this backdrop, it has been desired to develop drugs targeting PTP1B, for example, PTP1B inhibitors. However, the development is difficult to achieve under the present circumstance. Meanwhile, resveratrol contained in red wine has recently been reported to improve insulin sensitivity by reducing the expression level of PTP1B in the liver, indicating the possibility that a food ingredient can improve metabolic syndrome by controlling the activity or expression of PTP1B. In recent years, PTP1B has also been found to participate in the development of breast cancer and its metastasis to the lung, and this molecule has received attention again. Therefore, a food ingredient that inhibits the expression and activity of PTP1B is considered not only to improve metabolic syndrome but also to potentially exert great effects on disease involving PTP1B, such as cancer.

By use of the activity of the extract containing the compound (1) of the present invention inhibiting the expression and activity of PTP1B, the negative regulation of insulin effects, the mediation of intracellular signals resulting in the progression of breast cancer, etc., in which PTP1B is involved, can be controlled. The extract containing the compound (1) of the present invention can also be used for the development of a substance capable of negatively regulating glycosuria or breast cancer, from food-derived components can be achieved, in addition to the uses described above.

EXAMPLES

Examples below are intended to specifically show preferable embodiments of the present invention, and these Examples are not intended to limit the present invention.

Example 1

Aspergillus sp. PK-1 was inoculated into 200 g of secondarily rolled/dried green tea sterilized at 121° C. for 15 minutes in an autoclave, and cultured at 30° C. for 7 days.

The cultured tea leaves thus obtained are dried at 80° C. with hot air.

2.0 g of the dried tea leaves was pulverized using a mortar and subjected to an extraction treatment with 30 ml of a 60% aqueous ethanol solution. The extract thereby separated was subjected to HPLC (column: TOSOH ODS 80Ts (4.6 mm i.d.×250 mm), mobile phase: 1% acetic acid-$CH_3CN$ (90:10→20:80, in 30 min), flow rate: 0.6 ml/min., column temperature: 40° C., detection: 280 nm (UV)).

The obtained analysis results are as shown in Table 1.

TABLE 1

The contents (per % by dry weight) of components in various tea types are shown in the following table:

| Compound | PK-1 | AO-1 | SK-1 | KA-1 |
|---|---|---|---|---|
| | | % as dw | | |
| G | 1.05 | 8.52 | 9.95 | 5.21 |
| GC | 2.51 | 2.98 | 2.58 | 3.15 |
| EGC | 1.32 | 0.95 | 1.30 | 0.48 |
| C | 0.22 | 0.20 | 0.24 | 0.15 |
| Caffeine | 2.58 | 2.48 | 2.78 | 2.40 |
| EC | 0.03 | 0.05 | 0.07 | 0.05 |
| EGCG | 0.46 | 1.14 | 0.75 | 3.53 |
| ECG | 0.08 | 0.10 | 0.14 | 0.98 |
| Cis form of polyphenol of general formula (1) | 1.01 | 1.03 | 1.79 | 0.23 |
| Trans form of polyphenol of general formula (1) | 0.23 | 0.16 | 0.37 | 0.02 |

G: gallic acid
GC: (+)-gallocatechin
EGC: (−)-epigallocatechin
C: (+)-catechin
EC: (−)-epicatechin
EGCG: (−)-epigallocatechin 3-0-gallate
ECG: (−)-epicatechin 3-0-gallate Moreover, the novel substances thereby isolated were analyzed by magnetic resonance spectra, and these substances were consequently determined to be novel polyphenol derivatives having the chemical structure represented by the general formula (1), which were stereoisomers consisting of a cis form represented by the structural formula (2) and a trans form represented by the structural formula (3).

Furthermore, the novel polyphenol derivative represented by the structural formula (2) was confirmed to have the functions of decreasing visceral fat and increasing adiponectin, as a result of the test.

Example 2

A bud and leaves were plucked from each new shoot in a tea field (Yabukita; Shimizu ward, Shizuoka city, Shizuoka, Japan). Steaming, primary rolling and drying, crumpling, and secondary rolling and drying were performed according to the standard method of tea processing. Then, 1000 g thereof was stored in a refrigerator (−20° C.). 1000 g of the green tea thawed at room temperature was mixed with 100 g of precultured PK-1, and the mixture was cultured at approximately 25° C. for 2 weeks and 4 weeks with stirring once in a few days (treatment 1).

In this context, the precultured PK-1 was obtained by inoculating PK-1 into 50 g of secondarily rolled/dried green tea sterilized at 121° C. for 15 minutes in an autoclave, followed by culture at 30° C. for 7 days.

Subsequently, 2,000 ml of hot water (95° C.) was added to 1,000 g of the microbially fermented tea thus obtained by the culture, and the mixture was left standing at room temperature for 2 hours to perform the extraction treatment of an extract. After the extraction treatment, the tea leaves were filtered to obtain 750 ml of an extract.

750 ml of the obtained extract was mixed with 750 g of dextrin, and this slurry mixture was spray-dried.

Results of component analysis on the powder obtained by the spray drying are as shown in Table 2 below.

By virtue of its powdery form, the spray-dried product has favorable shelf life and is easily handleable and also convenient to add to other materials.

TABLE 2

| Component | Amount of each component in spray-dried product (g/100 g) |
|---|---|
| Gallic acid | 0.40 |
| GC | 0.36 |
| EGC | 0.92 |
| catechin | 0.07 |
| EC | 0.02 |
| EGCG | 0.16 |
| ECG | 0.05 |
| caffeine | 0.55 |
| Teadenol A | 0.12 |
| Teadenol B | 0.05 |
| Dextrin | 97.30 |

Next, rats were fed with feed supplemented with the spray-dried product of the present invention (hereinafter, referred to as a present invention spray-dried product (described as "SDP")), and raised. The results will be described.

(1) Preparation of Feed for Test

Three types were prepared according to the composition shown in Table 3: feed supplemented with 1% of the present invention spray-dried product (SDP) obtained above (1% supplemented group), feed supplemented with 3% thereof (3% supplemented group), and nonsupplemented feed (control group).

TABLE 3

| Composition of diet (g/kg diet) | | | |
|---|---|---|---|
| | Control group | 1% supplemented group | 3% supplemented group |
| Casein | 200 | 200 | 200 |
| Corn oil | 50 | 50 | 50 |
| Lard | 50 | 50 | 50 |
| corn starch | 150 | 150 | 150 |
| Cellulose | 50 | 50 | 50 |
| AIN-76 mineral mix | 35 | 35 | 35 |

TABLE 3-continued

| Composition of diet (g/kg diet) | | | |
|---|---|---|---|
| | Control group | 1% supplemented group | 3% supplemented group |
| AIN-76 vitamin mix | 10 | 10 | 10 |
| DL-methionine | 3 | 3 | 3 |
| Choline bitartrate | 2 | 2 | 2 |
| SDP* | 0 | 10 | 30 |
| Sucrose | 450 | 440 | 420 |

*SDP: Spray-dried product of Example of the present invention (2) Experimental Animals (Rats) and Raising Conditions The rats used were Otsuka Long-Evans Tokushima Fatty (OLETF) male rats (Otsuka Pharmaceutical Co., Ltd., Tokushima Research Institute) as rat models of obesity. Eighteen 4-week-old OLETF rats were separately placed in cages and preliminarily raised for 5 days with commercially available solid feed (Type NMF, Oriental Yeast Co., Ltd., Tokyo). Then, the rats were divided into 3 groups each involving 6 individuals.

The rats were given the feed (experimental diet) shown in Table 3 and raised for 28 days by pair-feeding.

During this period, the rats were allowed to freely drink water. For experimental diets, a purified diet according to the AIN-76 composition containing 5% each of corn oil and lard as dietary fats was used as a control diet.

Purified diets obtained by adding 1.0% or 3.0% SDP powder to the control diet and adjusting it to 100% with sucrose were used as test diets.

The raising environment was set to a light cycle involving room temperature (22 to 24° C.) for 12 hours (lighting from 8 a.m. to 8 p.m.). At the final day of the raising period, the rats were fasted overnight (0:00 to 9:00), and blood was collected from the abdominal aorta under pentobarbital anesthesia.

The adipose tissues (epididymal, perirenal, and mesenteric) and the liver were excised from each rat, and their weights were measured. Sera were prepared by centrifugation, and the concentration of each lipid and the concentration of adiponectin were measured using commercially available kits. Lipids were extracted from the liver by the method of Folch et al., and the concentration of each lipid was then measured. Moreover, a portion of the liver was homogenized and then fractionated into mitochondrial, cytosolic, and microsomal fractions by routine methods. A carnitine palmitoyl transferase (CPT) activity in the microsomal fraction and a fatty acid synthase (FAS) activity in the cytosolic fraction were determined.

(3) Statistical Processing

The obtained results were subjected to a significant difference test ($p<0.05$) by one-way analysis of variance (ANOVA) followed by the Tukey-kramer multiple analysis method.

(4) Results and Discussion (a) Body Weights and Food Consumptions

The body weights and food consumptions of the rats are shown in Table 4. Although no difference in food consumption and final body weight was confirmed among the groups, the group receiving 3% SDP tended to have a lighter final body weight than that of the other 2 groups.

Feed efficiency exhibited a lower value in the group receiving 3% SDP than in the other 2 groups.

(b) Weights of Liver and Adipose Tissues

Although the weight of the liver per unit body weight exhibited a slight decreasing tendency dependent on the consumption of the present invention spray-dried product (SDP), it was not significant effect. The weight of white adipose tissue was significantly decreased in a manner dependent on the SDP consumption, for all adipose tissues (epididymal, perirenal, and mesenteric) assayed this time (Table 4). This suggested that SDP used this time contained components having a body fat reducing effect.

TABLE 4

Influence of SDP consumption on amount of body weight increased, food consumption, and weight of each tissue

|  | Control group | 1% supplemented group | 3% supplemented group |
|---|---|---|---|
| Initial body weight (g) | 117 ± 5 | 117 ± 3 | 116 ± 4 |
| Final body weight (g) | 307 ± 14 | 320 ± 2 | 295 ± 6 |
| Food consumption (g/day) | 20.6 ± 0.1 | 20.6 ± 0.1 | 19.6 ± 0.4 |
| Feed efficiency (g gain/g diet) | $0.364 \pm 0.006^a$ | $0.365 \pm 0.006^a$ | $0.339 \pm 0.004^b$ |
| Tissue weight (g/100 g) |  |  |  |
| Liver | 4.43 ± 0.28 | 4.08 ± 0.06 | 3.99 ± 0.08 |
| Epididymal adipose tissue | $1.77 \pm 0.05^a$ | $1.48 \pm 0.03^b$ | $1.31 \pm 0.05^c$ |
| Perirenal adipose tissue | $2.94 \pm 0.12^a$ | $2.30 \pm 0.07^b$ | $2.00 \pm 0.10^b$ |
| Mesenteric adipose tissue | $1.52 \pm 0.07^a$ | $1.22 \pm 0.03^b$ | $0.985 \pm 0.045^c$ |

Mean ± SE (n = 6), there was a significant difference between opposite signs. ($p < 0.05$)

(c) Serum Component Analysis

The serum total cholesterol concentration did not exhibit a constant tendency dependent on the SDP consumption; however, it tended to be high in the 3% supplemented group (Table 5). The serum HDL-cholesterol concentration tended to be high in a manner dependent on the SDP consumption and exhibited a significantly higher value in the 3% supplemented group than in the other 2 groups.

Although the influence of SDP consumption on the serum triglyceride concentration was not clearly defined, the serum free fatty acid concentration exhibited a significantly high value in the 3% supplemented group. This indicated that enhanced lipolysis (release of free fatty acids from adipose tissues) in adipose tissues might be responsible for the reduction in the weight of each adipose tissue, shown in Table 2, in the groups receiving SDP.

The serum adiponectin concentration was confirmed to have an increasing tendency dependent on the SDP consumption, which was, however, not statistically significant change (Table 5).

TABLE 5

Influence of SDP consumption on concentrations of serum lipids and adiponectin

|  | Control group | 1% supplemented group | 3% supplemented group |
|---|---|---|---|
| Total cholesterol (mg/dL) | $167 \pm 6^{ab}$ | $147 \pm 6^a$ | $185 \pm 7^b$ |
| HDL-cholesterol (mg/dL) | $82.3 \pm 5.1^a$ | $85.6 \pm 2.4^a$ | $101.1 \pm 3.3^b$ |
| HDL/total cholesterol ratio | $0.492 \pm 0.022^a$ | $0.586 \pm 0.027^b$ | $0.548 \pm 0.017^{ab}$ |
| Phospholipid (mg/dL) | $264 \pm 8^a$ | $220 \pm 9^b$ | $239 \pm 14^{ab}$ |

TABLE 5-continued

Influence of SDP consumption on concentrations of serum lipids and adiponectin

|  | Control group | 1% supplemented group | 3% supplemented group |
|---|---|---|---|
| Triglyceride (mg/dL) | 97.5 ± 10.9 | 85.0 ± 10.4 | 93.2 ± 16.8 |
| Free fatty acid (mmol/L) | $484 \pm 49^a$ | $493 \pm 24^a$ | $641 \pm 33^b$ |
| Adiponectin (µg/mL) | 4.35 ± 0.18 | 4.97 ± 0.31 | 5.32 ± 0.51 |

Mean ± SE (n = 5 or 6), there was a significant difference between opposite signs. ($p < 0.05$)

Reduction in the weight of each adipose tissue caused by SDP consumption was confirmed in Table 4. This suggested that the adipocytes were decreased in size, and seemed to be related to increase in serum adiponectin concentration. Since the serum adiponectin concentration increasing effect, albeit slight, was confirmed, the SDP components were shown to serve as potential factors preventing lifestyle-related disease.

(d) Liver Lipid Concentrations and Enzyme Activities

The liver triglyceride concentration was decreased in a manner dependent on the SDP consumption and exhibited a significantly lower value in the 3% supplemented group than in the control group (Table 6).

TABLE 6

Influence of SDP consumption on liver lipid concentrations and fatty acid metabolism-related enzyme activities

|  | Control group | 1% supplemented group | 3% supplemented group |
|---|---|---|---|
| Lipid concentration (mg/g liver) |  |  |  |
| Cholesterol | 2.42 ± 0.10 | 2.47 ± 0.08 | 2.56 ± 0.09 |
| Phospholipid | $31.0 \pm 0.5^a$ | $31.9 \pm 0.5^{ab}$ | $34.0 \pm 0.6^b$ |
| Triglyceride | $18.5 \pm 1.9^a$ | $13.7 \pm 1.5^{ab}$ | $12.4 \pm 0.5^b$ |
| Enzyme activity (nmol/min/mg protein) |  |  |  |
| FAS*[1] | $27.8 \pm 2.2^a$ | $22.8 \pm 0.9^{ab}$ | $17.5 \pm 1.2^b$ |
| CPT*[2] | 4.00 ± 0.32 | 4.42 ± 0.49 | 4.28 ± 0.24 |

*[1]FAS: Fatty acid synthase (liver cytosolic fraction)
*[2]CPT: Carnitine palmitoyl transferase (liver mitochondrial fraction)
Mean ± SE (n = 5 or 6), there was a significant difference between opposite signs. ($p < 0.05$)

Likewise, the FAS activity in the liver cytosol was also reduced in a manner dependent on the SDP consumption (Table 6), and this seemed to be a cause of reduction in liver triglyceride concentration.

On the other hand, no difference in the CPT activity in the liver mitochondrion was observed among the groups. In general, it is known that the fatty acid β oxidation ability of the liver is influenced by adiponectin. However, it was presumed that increase in serum adiponectin concentration caused by SDP did not influence the liver CPT activity under these experimental conditions.

In this experiment, the effects of decreasing adipose tissue weights and reducing liver triglyceride concentrations by SDP consumption were confirmed, and increase, albeit slight, in serum adiponectin concentration was also observed.

These results showed the release of free fatty acids from adipose tissues and the effect of reducing fatty acid synthesis ability in the liver, as a cause thereof.

Thus, it was confirmed in this experiment that the feed efficiency was significantly reduced in the 3% supplemented group.

Example 3

Component Analysis by HPLC

Figure 2:
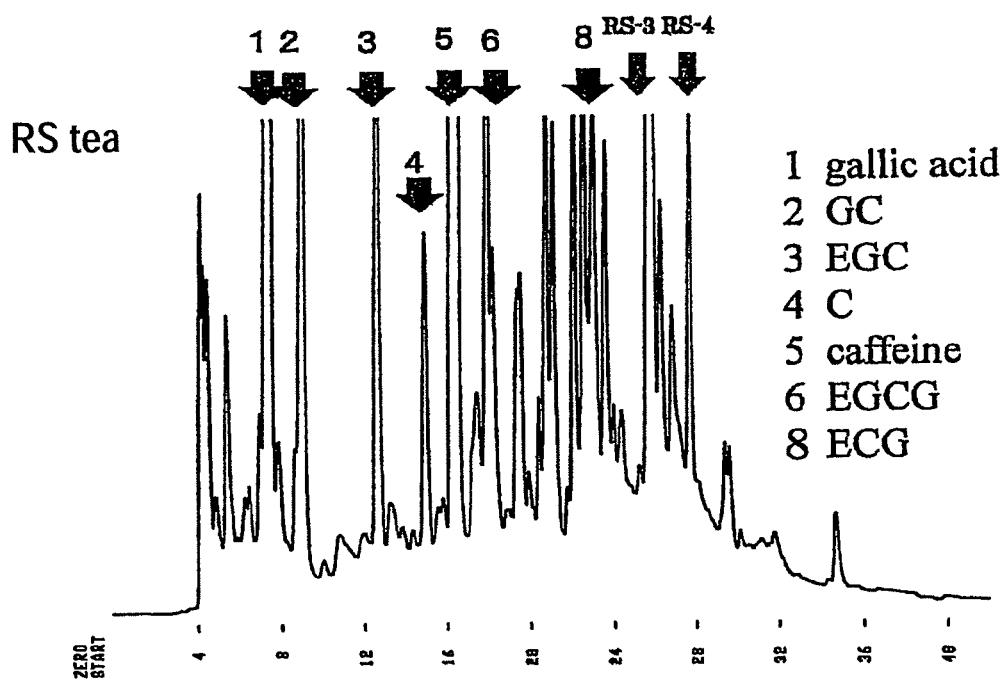
FIG. 2 is an HPLC profile of microbially fermented tea (RS tea). In the diagram,
- 1: Peak of gallic acid,
- 2: Peak of (+)-gallocatechin (GC),
- 3: Peak of (−)-epigallocatechin (EGC),
- 4: Peak of (+)-catechin (C),
- 5: Peak of caffeine,
- 6: Peak of (−)-epigallocatechin 3-O-gallate (EGCG),
- 8: Peak of (−)-epicatechin 3-O-gallate (ECG),
- RS-3: Peak of a cis form of a polyphenol derivative (compound (2)) according to the present invention, and
- RS-4: Peak of a trans form of a polyphenol derivative (compound (3)) according to the present invention.

Tea leaves (RS tea) subjected to a fermentation treatment with *Aspergillus* sp. (PK-1, FERM P-21280) were used. Hot water (distilled water, 30 ml) of 80° C. was added to dried fermented tea leaves (4.5 g), and the mixture was left standing overnight at room temperature to perform an extraction treatment. After filtration, an extract (filtrate) was obtained. The filtrate (2.5 µl) was subjected to HPLC analysis. Conditions used in the HPLC analysis are as follows:
Column: TOSOH ODS 80Ts (4.6 mm i.d.×250 mm)
Mobile phase: 1 mM aqueous TBA (tetrabutylammonium) solution (pH 2.9)-$CH_3CN$ (90:10→20:80, in 30 min) [TBA solution was adjusted to pH 2.9 with an aqueous solution containing approximately 0.1% acetic acid],
flow rate: 0.6 ml/min., column temperature: 40° C.,
detection: 280 nm (UV)
The HPLC elution pattern is shown in FIG. 2.
In FIG. 2, the contents (per % by dry weight) of various components in the RS tea were as follows:
1: gallic acid (1.09% dw)
2: GC [(+)-gallocatechin] (3.96% dw)
3: EGC [(−)-epigallocatechin] (2.14% dw)
4: C [(+)-catechin] (0.21% dw)
5: caffeine (1.92% dw)
6: EGCG [(−)-epigallocatechin 3-O-gallate] (0.24% dw)
8: ECG [(−)-epicatechin 3-O-gallate] (0.14% dw)
RS-3: 0.54% dw [compound (2)]
RS-4: 0.06% dw [compound (3)]
In this context, EC [(−)-epicatechin] (0.49% dw) is not shown in FIG. 2.
[Component Analysis by LC-TOF/MS]
Components in microbially fermented tea (RS tea) subjected to a fermentation treatment with *Aspergillus* sp. PK-1 as in Example 1 were compared with components in various tea types (green tea, oolong tea, black tea, and pu-erh tea made in China). Hot water (distilled water, 30 ml) of 80° C. was added to each of these 5 tea types (e.g., 4.5 g each), and each mixture was left standing overnight at room temperature to perform an extraction treatment.
After filtration, extracts (filtrates) were obtained. Component analysis was conducted by LC-TOF/MS. HPLC and TOF/MS conditions used in the LC-TOF/MS analysis are as follows:
HPLC (Agilent 1100 series):
Column: ZORBAX Eclipse Plus C18, 2.1 mm in inside diameter×100 mm in length, particle size: 3.5 µm
Column temperature: 40° C., flow rate: 0.2 mL/min
Mobile phase: 0.1% formic acid+10 mM $AcONH_4$ (A), $CH_3CN$ (B)
Gradient conditions: A:B (time)
95:5 (0 min)→50:50 (30 min)→10:90 (40 min)→10:90 (45 min)
[→95:5 (50 min)→95:5 (60 min)]
TOF/MS (Agilent G 1969A)
Ionization: ESI, Positive
Dry gas: $N_2$, 350° C., 10 L/min
Nebulizer: $N_2$, 50 psig
Capillary voltage: 4000 V
Fragmentor voltage: 100 V
Scan range: 80 to 1,200 (m/Z)
Reference mass: 121.0509 and 922.0098

The obtained results are shown in FIGS. 3 and 4. The component RS-3 shown in FIG. 4B is one of the components specifically contained in the RS tea and was presumed to be a novel substance. This component was finally determined to correspond to an isolate A described below. RS-3 as well as RS-1, RS-2, and RS-2', which had the same composition as that of RS-2, appeared to be components specifically contained in the RS tea.

Example 4

Extraction and Isolation of Novel Components (Compounds (2) and (3)) by Column Chromatography

[Treatment 1]
Since the component RS-3 (i.e., isolate A) was presumed to be a novel substance, an attempt was made to extract and isolate this component from tea leaves. During the course of this isolation, an isolate B having the same composition as that of the isolate A was also isolated. The procedures of isolating these novel components will be shown below.

Tea leaves subjected to a fermentation treatment with *Aspergillus* sp. (PK-1, FERM P-21280) as described in Example 1 were used. 207 g of dried tea leaves was subjected to overnight extraction with 80% ethanol (800 ml), followed by filtration through gauze. The residual tea leaves were subjected to overnight extraction with 800 ml of hot water of 80° C., followed by filtration again. Each filtrate was concentrated with an evaporator and then applied to a DIAION column (4×33 cm, Mitsubishi Chemical Corporation), followed by elution with methanol-water mixed solutions (0%-20%-40%-60%-100%, 500 ml each). The 40% methanol-eluted fraction was concentrated and then applied to a Sephadex LH20 column (4×50 cm, Pharmacia Corporation), followed by elution with a 60% aqueous methanol solution to obtain two fractions.

The isolate A (compound (2), 290 mg) was obtained from the fraction 1 by crystallization (solvent: water).

The fraction 2 was applied to Sephadex LH20 (4×32 cm, Pharmacia Corporation), followed by elution with an 80% aqueous ethanol solution to obtain a fraction containing RS-4. This fraction was concentrated and then applied to Preparative C18 (3×20 cm, Waters Corporation), followed by elution with methanol-water mixed solutions (0%-200-400-60%-1000, 300 ml each) to obtain a 20% methanol-eluted fraction. This fraction was concentrated and then applied to Fuji-gel ODS (3×19 cm, Fujigel Hanbai Co., Ltd.), followed by elution with methanol-water mixed solutions (0%-20%-40%-60%-100%, 300 ml each). The 20% methanol-eluted fraction was concentrated and crystallized (solvent: water) to obtain the isolate B (compound (3), 43 mg), which corresponded to the component RS-4.
[Treatment 2]
Tea leaves subjected to a fermentation treatment with *Aspergillus* sp. (PK-1, FERM P-21280) as described above were used. Dried tea leaves (207 g) were subjected to extraction with 80% ethanol (800 ml) at room temperature for 12 hours. The obtained extract was vacuum-concentrated. Next, the obtained concentrated extract (37 g) was applied to a DIAION HP20SS column (Mitsubishi Chemical Corporation), followed by elution with methanol-water mixed solutions (0:0→100:0).

Four fractions were obtained: fraction 1 (5 g), fraction 2 (1 g), fraction 3 (17 g), and fraction 4 (3 g). The fraction 3 was applied to a Sephadex LH20 column (Pharmacia Corporation), followed by elution with a 60% aqueous methanol solution to obtain two fractions [fraction 3-1 and fraction 3-2].

The fraction 3-1 (13 g) was applied to an ODS-G3 column (Fujigel Hanbai Co., Ltd.), followed by a stepwise elution treatment with $H_2O$ and methanol to obtain the isolate A (compound (2), 390 mg).

The fraction 3-2 (2.3 g) was applied to a Sephadex LH20 column (Pharmacia Corporation), followed by elution with 80% aqueous methanol solution. Next, the eluted fraction was applied to an ODS-G3 column (Fujigel Hanbai Co., Ltd.), followed by a stepwise elution treatment with $H_2O$ and methanol. The eluted fraction was further applied to Preparative $C_{18}$ 125 Å (Waters Corporation), followed by a stepwise elution treatment with $H_2O$ and methanol to obtain the isolate B (compound (3), 88 mg).

The chemical structure of the isolate A was determined by mass spectrometry (MS), infrared spectroscopy (IR), nuclear magnetic resonance analysis (NMR), etc. As a result, the isolate A was identified as a compound having a chemical structure represented by the following formula:

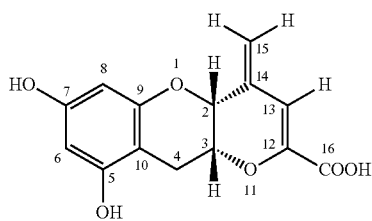

[Formula 6]

This compound was designated as teadenol A and could be confirmed to be a novel compound as described above.

Isolate A: white crystal, mp 235-240° C. (decomposed), $[\alpha]_D^{21}$+467.8° (c 0.15, DMSO), m/z 276.0638, $C_{14}H_{12}O_6$, NMR (in DMSO-$d_6$): see Table 7.

IR (KBr) $cm^{-1}$: 3420, 1700, 1632, 1611, 1386, 1273, 1260, 935.

TABLE 7

| | NMR (mDMSO-$d_6$) | | |
|---|---|---|---|
| Position | $\delta_C$  $\delta_H$ | HMBC ($^1H$—$^{13}C$) | NOE ($^1H$—$^1H$) |
| 2 | 70.9  4.56 (1H, s) | C-13, 14, 15 | H-3, 4, 13, 15 |
| 3 | 70.8  4.36 (1H, m) | C-2, 10 | H-2, 4 |
| 4 | 24.1  2.76 (2H, m) | C, 2, 3, 5, 10 | H-2, 3, 8 |
| 5 | 156.3 — | | |
| 6 | 95.6  5.91 (1H, d, J = 2.3 Hz) | C-8, 10 | H-8, 15 |
| 7 | 156.6 — | | |
| 8 | 94.2  5.64 (1H, d, J = 2.3 Hz) | C-6, 10 | H-4, 6 |
| 9 | 154.7 — | | |
| 10 | 96.9 — | | |
| 12 | 144.1 — | | |
| 13 | 110.2  6.51 (1H, d, J = 0.9 Hz) | C-2, 12, 14, 16 | H-2, 15 |
| 14 | 136.5 — | | |
| 15 | 118.0  5.27 (1H, br. s) | C-2, 13, 14 | H-2, 6, 13, 15 |
|  | 5.39 (1H, brs) | C-2, 13, 14 | H-2, 13, 15 |
| 16 | 163.2 — | | |
| 5-OH | 9.00 (1H) | C-5, 6, 10 | |
| 7-OH | 9.33 (1H) | C-6, 7, 8 | |

The isolate B had the same molecular formula $C_{14}H_{12}O_6$ as that of teadenol A and was identified as a compound having a chemical structure represented by the following formula:

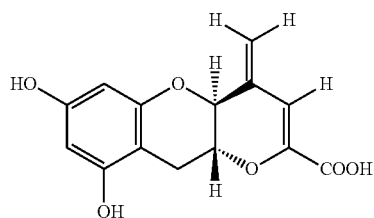

[Formula 7]

This compound was designated as teadenol B.

Isolate B: gray-white crystal, mp 258-275° C. (decomposed), $[\alpha]_D^{20}$−27.7° (c 0.18, MeOH), m/z 276.0640, $C_{14}H_{12}O_6$, NMR (in $CD_3OD$): see Table 8.

TABLE 8

| | NMR (in $CD_3OD$) | | |
|---|---|---|---|
| Position | $\delta_C$  $\delta_H$ | HMBC ($^1H$—$^{13}C$) | NOE ($^1H$—$^1H$) |
| 2 | 73.2  4.36 (1H, d, J = 10.5 Hz) | C-14 | H-3, 15 |
| 3 | 75.0  4.01 (1H, m) | C-2, 4 | H-2, 4 |
| 4 | 27.1  2.66 (1H, dd, J = 10.3, 15.7 Hz) | C-3, 9, 10 | H-3, 4 |
|  | 3.20 (1H, dd, J = 5.9, 15.7 Hz) | C-2, 3, 5, 9, 10 | H-3, 4 |
| 5 | 157.7 — | | |
| 6 | 96.9  5.96 (1H, d, J = 2.3 Hz) | C-5, 7, 8, 10 | |
| 7 | 158.2 — | | |
| 8 | 95.6  5.91 (1H, d, J = 2.3 Hz) | C-7, 9, 10 | |
| 9 | 156.0 — | | |
| 10 | 100.0 — | | |
| 12 | 145.0 — | | |
| 13 | 113.2  6.63 (1H, s) | C-2, 16 | H-15 |
| 14 | 138.6 — | | |
| 15 | 113.3  5.33 (1H, s) | C-2, 13 | H-2, 13, 15 |
|  | 5.51 (1H, s) | C-2, 13, 14 | H-2, 13, 15 |
| 16 | 166.0 | | |

[Preparation of Teadenol]

EGCG [(−)-epigallocatechin 3-O-gallate] (purchased from Sigma-Aldrich Corporation, 16 mg) was dissolved in water (20 ml), and this solution was autoclaved (121° C., 15 min). This autoclave treatment converts almost 50% of EGCG molecules to C-2 epimers thereof. *Aspergillus* sp. (PK-1, FERM P-21280) subcultured in a solid medium (potato dextrose agar) was inoculated (1 cm×1 cm piece) into the autoclaved EGCG-containing solution (mixture of EGCG and GCG). The obtained mixture solution was cultured on a rotary shaker (60 rpm) at 25° C. under dark conditions. After 2-week culture, components in the solution obtained by the culture treatment were analyzed. This solution was filtered through a Millipore filter (0.45 μm) and then subjected to HPLC. HPLC conditions used in the analysis are as follows:

Column: TOSOH ODS 80Ts (4.6 mm×250 mm, Tosoh Corporation), mobile phase: 0.1% formic acid-$CH_3CN$ (9:1→1:4 in 30 min), flow rate: 0.6 ml/min, column temperature: 40° C., detection: 80 nm (UV), retention times (min) of compounds: EGCG (18.7), GCG (19.8), teadenol A (24.9), and teadenol B (27.7). 62.5±15.6 μg of teadenol A was detected, and 24.4±7.3 μg of teadenol B was detected (mean±SD of 3 experiments).

Example 5

Adiponectin Secretion Promoting Effect

3T3-L1 adipocytes can be allowed to grow and maintained in a 5% $CO_2$ environment in high-glucose DMEM containing 50 U/ml penicillin, 50 μg/ml streptomycin, and 10% FCS. The 3T3-L1 cells were subcultured in a dish of 3.5 cm in diameter until confluent and then sufficiently differentiated into adipocytes by culture for another 2 days in the presence of insulin (10 μg/ml), dexamethasone (0.25 μM), and IBMX (3-isobutyl-1-methylxanthine) (0.5 mM). Teadenol A (10 μM) or DMSO (vehicle control) was added to the sufficiently differentiated 3T3-L1 adipocytes, and each culture supernatant was collected after 8, 24, 32, and 48 hours. The amount of adiponectin secreted was determined by Western blotting method. The results are shown in FIG. 5. This diagram shows a typical Western blot pattern and shows results of three runs. The results are summarized in Table 9.

TABLE 9

Summary

| 3 runs | Sample name | | Mean | Standard error |
|---|---|---|---|---|
| 1 | Teadenol A | 8 h | 166.00 | 34.12 |
| 2 | Teadenol A | 24 h | 214.67 | 39.84 |
| 3 | Teadenol A | 32 h | 153.33 | 22.60 |
| 4 | Teadenol A | 48 h | 147.67 | 12.91 |
| 5 | 100% DMSO | 8 h | 100.00 | 3.82 |
| 6 | 100% DMSO | 24 h | 100.00 | 13.77 |
| 7 | 100% DMSO | 32 h | 100.00 | 6.20 |
| 8 | 100% DMSO | 48 h | 100.00 | 10.13 |

Figure 6:
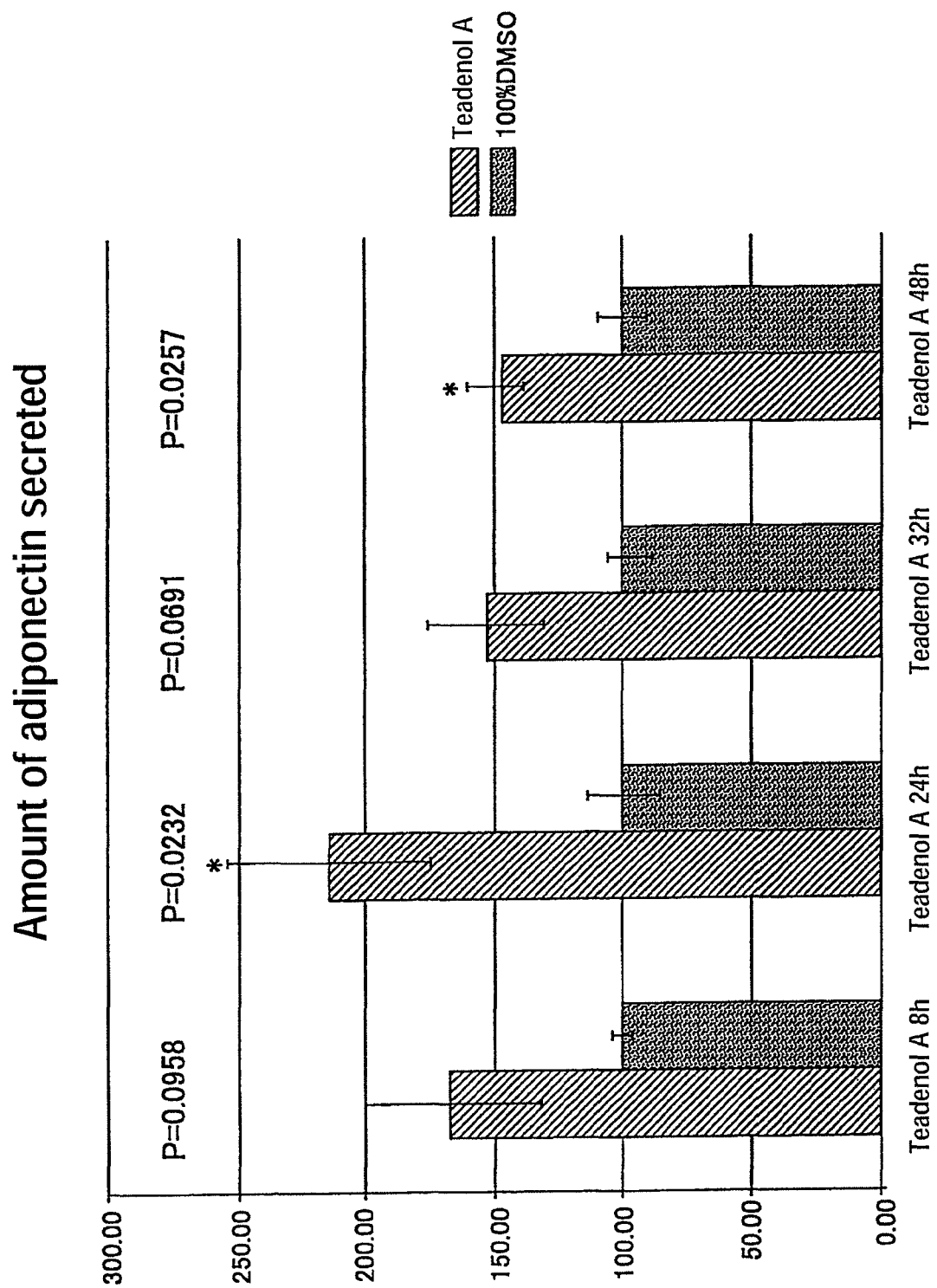
FIG. 6 is assay results of the adiponectin secretion promoting activity of teadenol A and shows the relationship between the amount of adiponectin secreted and a time lapsed after addition of teadenol A.

The relationship between the amount of adiponectin secreted and a time lapsed after addition of teadenol A is shown in FIG. 6. In FIG. 6, "teadenol" represents teadenol A. The addition of teadenol was confirmed to be effective for the adiponectin secretion promoting activity with statistically significant difference in the samples after 24 and 48 hours. Likewise, the addition of teadenol B can be confirmed to be effective for the adiponectin secretion promoting effect.

Example 6

PTP1B Expression Inhibitory Effect

Teadenol A (10 μM) or DMSO (vehicle control) was added to the sufficiently differentiated 3T3-L1 adipocytes. After culture for 8, 24, 32, and 48 hours, the cells were collected, and the amount of PTP1B secreted and the amount of α-tubulin were determined by Western blotting method. The results are shown in FIGS. 7 to 11. In these diagrams, "teadenol" represents teadenol A. Each of FIGS. 7 to 9 shows a typical Western blot pattern. The results of 3 runs are summarized in FIG. 10.

Figure 11:
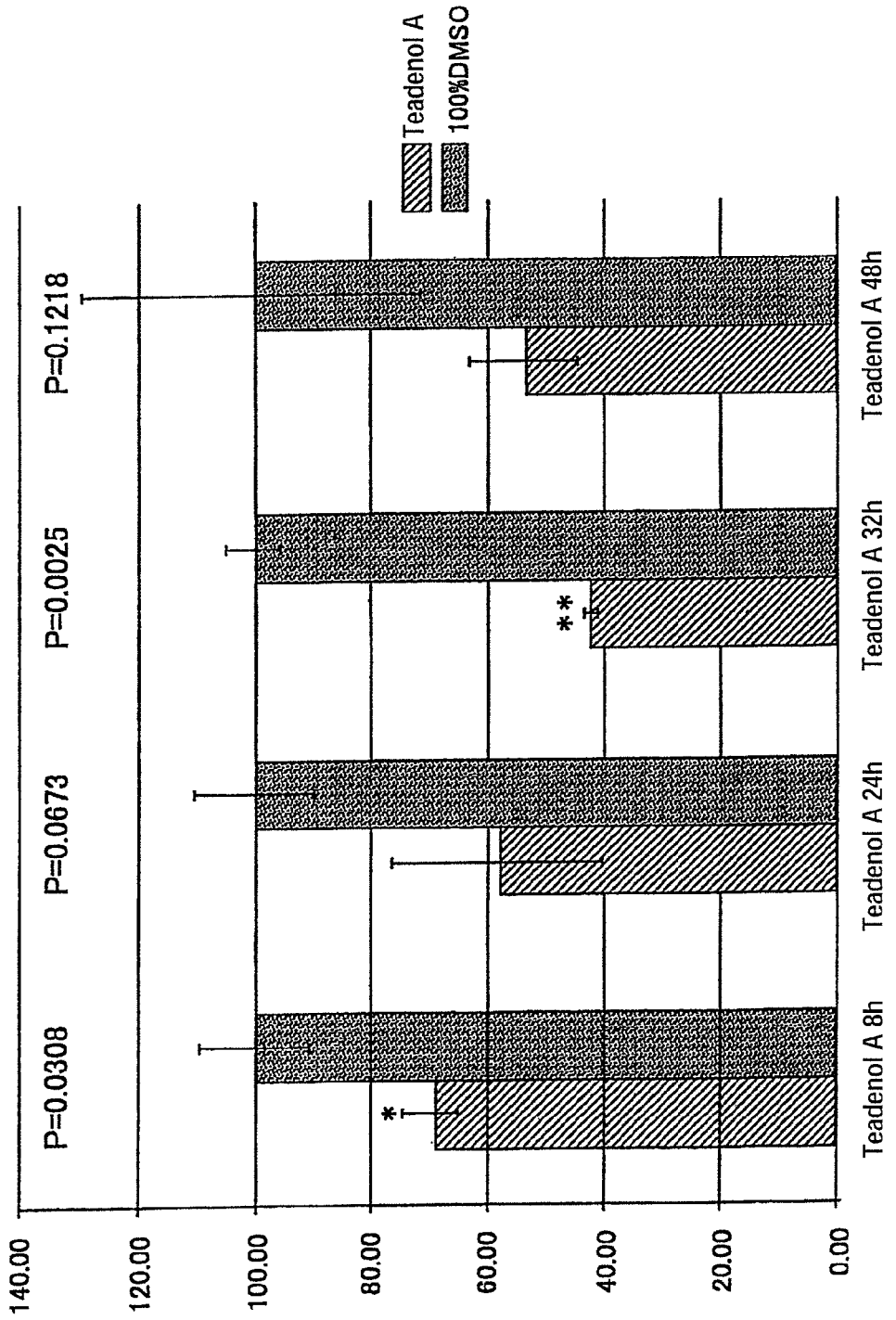
FIG. 11 is assay results of the PTP1B expression inhibitory activity of teadenol A.

The relationship between a PTP1B expression level and a time lapsed after the addition of teadenol A is shown in FIG. 11. The addition of teadenol A was confirmed to be effective for the PTP1B expression inhibitory activity with statistically significant difference in the samples after 32 hours. Likewise, the addition of teadenol B can be confirmed to be effective for the PTP1B expression inhibitory effect.

INDUSTRIAL APPLICABILITY

An extract containing a novel polyphenol derivative according to the present invention is expected to be used as a functional substance exhibiting specific physiologically active effects, together with various extracts, i.e., gallic acid, gallocatechin, epigallocatechin, catechin, epicatechin, epigallocatechin gallate, epicatechin gallate, and kaempferol triglycoside.

Accordingly, the functional microbially fermented tea extract containing the polyphenol derivative obtained in the present invention can be used in a processed food, a seasoning, a health supplement (e.g., a supplement), animal feed (e.g., a pet food), a cosmetic, etc.

REFERENCE SIGNS LIST

1: Peak of gallic acid
2: Peak of gallocatechin
3: Peak of epigallocatechin
4: Peak of catechin
5: Peak of caffeine
6: Peak of epigallocatechin gallate
7: Peak of kaempferol triglycoside
8: Peak of epicatechin gallate
A: Peak of a cis form of a polyphenol derivative according to the present invention
B: Peak of a trans form of a polyphenol derivative according to the present invention

The invention claimed is:

1. A method for producing a concentrated microbially fermented tea extract, the method comprising:
    a) culturing a tea leaf with *Aspergillus* sp. (PK-1) or *Eurotium* sp. (KA-1) to obtain a microbially fermented tea leaf;
    b) extracting the microbially fermented tea leaf to obtain a microbially fermented tea extract comprising a polyphenol represented by the following general formula (I):

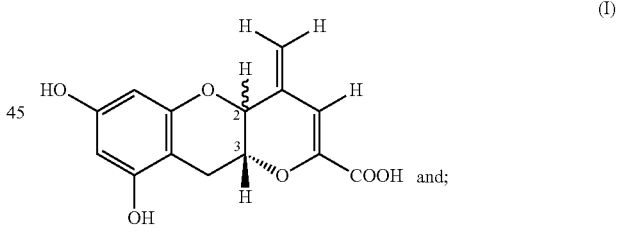

(I)

c) adding a composition consisting of the polyphenol represented by the general formula (I) to the microbially fermented tea extract to obtain a concentrated microbially fermented tea extract.

2. The method for producing a concentrated microbially fermented tea extract according to claim 1, wherein the tea leaf is cultured with *Aspergillus* sp. (PK-1).

3. The method for producing a concentrated microbially fermented tea extract according to claim 1, wherein the tea leaf is cultured with *Eurotium* sp. (KA-1).

* * * * *